(12) United States Patent
Kim et al.

(10) Patent No.: US 12,714,835 B2
(45) Date of Patent: Aug. 25, 2026

(54) SYSTEM FOR DETERMINING LOCATION INSIDE BODY

(71) Applicant: CHONNAM NATIONAL UNIVERSITY HOSPITAL, Gwangju (KR)

(72) Inventors: Ja Hae Kim, Gwangju (KR); Yun Chul Park, Gwangju (KR)

(73) Assignee: CHONNAM NATIONAL UNIVERSITY HOSPITAL, Gwangju (KR)

( * ) Notice: Subject to any disclaimer, the term of this patent is extended or adjusted under 35 U.S.C. 154(b) by 944 days.

(21) Appl. No.: 17/288,652

(22) PCT Filed: Oct. 28, 2019

(86) PCT No.: PCT/KR2019/014293
§ 371 (c)(1),
(2) Date: Apr. 26, 2021

(87) PCT Pub. No.: WO2020/085883
PCT Pub. Date: Apr. 30, 2020

(65) Prior Publication Data

US 2022/0008696 A1 Jan. 13, 2022

Related U.S. Application Data

(60) Provisional application No. 62/880,693, filed on Jul. 31, 2019.

(30) Foreign Application Priority Data

Oct. 26, 2018 (KR) ........................ 10-2018-0129274
Sep. 27, 2019 (KR) ........................ 10-2019-0119581

(51) Int. Cl.
*A61M 25/10* (2013.01)
*A61B 6/12* (2006.01)
*A61K 51/12* (2006.01)

(52) U.S. Cl.
CPC ........... *A61M 25/1018* (2013.01); *A61B 6/12* (2013.01); *A61K 51/1282* (2013.01); *A61M 2025/1079* (2013.01)

(58) Field of Classification Search
CPC ...... A61M 25/1018; A61M 2025/1079; A61M 25/09; A61M 2025/1052; A61M 25/0105;
(Continued)

(56) References Cited

U.S. PATENT DOCUMENTS 5,879,282 A 3/1999 Fischell et al.
6,210,312 B1 * 4/2001 Nagy .................... A61M 25/10 600/3

(Continued)

FOREIGN PATENT DOCUMENTS

KR 10-2007-0106711 A 11/2007
WO WO 01/14011 A1 3/2001
WO WO 2006/043276 A2 4/2006

OTHER PUBLICATIONS

International Search Report for PCT/KR2019/014293 mailed on Feb. 6, 2020.

(Continued)

*Primary Examiner* — Anh Tuan T Nguyen
*Assistant Examiner* — Dean N Edun
(74) *Attorney, Agent, or Firm* — The PL Law Group, PLLC

(57) ABSTRACT

A system for in vivo location determination of a balloon catheter according to an embodiment of the present disclosure includes a detector configured to detect proximity of a radioactive material, a guide wire provided to be inserted
(Continued)

into a body, an intermediate member which has a radioactive material detected by the detector, and is configured to be inserted into the body along the guide wire to set an insertion length at which the radioactive material is detected by the detector, and a balloon catheter which is inserted into the body along the guide wire, and is inserted into the body by the set insertion length.

3 Claims, 9 Drawing Sheets

(58) Field of Classification Search
CPC .......... A61M 25/10; A61B 6/12; A61B 34/20; A61B 90/00; A61K 51/1282
See application file for complete search history.

(56) References Cited

U.S. PATENT DOCUMENTS

2002/0022799 A1 2/2002 Apple et al.
2002/0156515 A1 10/2002 Jang et al.
2003/0100849 A1* 5/2003 Jang .................... A61M 25/104 600/585
2003/0192557 A1 10/2003 Krag et al.
2004/0015075 A1* 1/2004 Kimchy ............... A61B 6/5247 600/431
2008/0262473 A1* 10/2008 Kornblau ................. A61B 5/06 604/529
2010/0094266 A1* 4/2010 Travish .................. H01J 35/14 606/15
2011/0164724 A1* 7/2011 Ohta ........................ A61B 6/06 378/97
2018/0303445 A1* 10/2018 Subramanian ......... A61B 6/563

OTHER PUBLICATIONS

Yunchul Park et al., “Gamma probe-guided confirmation of balloon placement in endovascular procedures”, Journal of Trauma Acute Care Surgery, Vo.86 (6), pp. 994-1000, 2019, Retrieved from , DOI: 10.1097/TA.0000000000002238.

* cited by examiner

110

130

120

150

(A)

(B)

(A)

(B)

(A)

(B)

(A)

(B)

SYSTEM FOR DETERMINING LOCATION INSIDE BODY

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/014293, filed Oct. 28, 2019, which claims priority to the benefit of Korean Patent Application No. 10-2018-0129274 filed in the Korean Intellectual Property Office on Oct. 26, 2018, U.S. Patent Application No. 62/880,693 filed on Jul. 31, 2019 and Korean Patent Application No. 10-2019-0119581 filed in the Korean Intellectual Property Office on Sep. 27, 2019, the entire contents of which are incorporated herein by reference.

BACKGROUND

Technical Field

The present invention relates to a detection technology for determination of the location of a medical device inserted into a body from outside the body, and more specifically, to a balloon inflation composition for in vivo location determination of a balloon catheter, which allows accurate and safe determination of the location of the balloon catheter inserted into the body from outside the body, and a system for in vivo location determination of a balloon catheter including the same.

Background Art

In general, a balloon catheter is used to inflate a narrow or obstructed region of the coronary artery, esophagus, Eustachian tube, or ureteropelvic junction of kidneys. After inflating the balloon with a contrast medium, when a fluoroscopy image is obtained, the location and inflation process of the balloon may be determined.

Currently, bleeding is the most common cause of preventable death in trauma patients. Among the causes of bleeding, non-compressive trunk bleeding is very fatal, and its fatality rate is up to 18% to 45%. In patients with severe bleeding, a classical method of clamping the aorta from an outside to stop the bleeding has been used. However, this method has disadvantages that it is difficult to implement immediately in an emergency scene, and may be implemented only by an experienced doctor in a situation in which many types of equipment are available.

Recently, the balloon catheter is also used to temporarily block a large blood vessel upon bleeding in patients with truncal hemorrhage. That is, in order to control the non-compressive trunk bleeding, there is a new method of stopping the bleeding from the large blood vessel in the body by introducing a balloon catheter into the blood vessel to inflate the balloon, and good research results regarding the method have been suggested. In fact, it has been demonstrated that a technology of controlling the bleeding by introducing a balloon catheter into the blood vessel and inflating the balloon in the proximal portion of the bleeding lesion has a hemostatic effect superior to the classical method in many studies conducted on animals and humans.

However, when the balloon catheter is inserted into the body, it is difficult to determine the exact location of the balloon catheter outside the body. To determine the same, there is a method of predicting the location of the balloon catheter using an external boundary mark. However, in the case of a patient whose location of the blood vessel causing bleeding and the external boundary mark do not match, it is difficult to accurately position the balloon at the bleeding lesion. In order to solve the above-described problems, several different methods have been proposed to determine the exact location of the balloon as follows. First, a method of determining the location of an image guide for the location of the balloon obtained by fluoroscopy or static radiography is generally widely recommended, and is also recommended by manufacturing companies. However, this method has a disadvantage that it can only be used in hospital environments equipped with the fluoroscopy devices. Second, an image guidance verification method using ultrasound has also been proposed. However, it is not possible to reveal the abdominal aorta in obese patients or patients with a lot of air in the small intestine by the ultrasound test. Further, in the case of the ultrasound test, since test results vary greatly depending on the experience of an operator performing the ultrasound evaluation, the ultrasound test particularly performed in an emergency situation may easily cause a mistake of the operator. Also, in ultrasound, it is necessary to determine the location of a REBOA catheter tip. However, the catheter tip may be obscured by fragments and air, which is often seen in the majority of patients. Third, as another method for determining the location of the balloon, there is also a thermal imaging method. However, according to the previous studies, since an infrared imaging device needs to take images of the anatomical target for 5 to 10 minutes (Barron 2018), followed by measuring at least 2 points on the lesion, and then additionally calculating the results of the measurements by the researcher, there is a disadvantage that it takes a lot of time.

A gamma probe is a portable surgical radioisotope detector which is capable of detecting photon radiation such as gamma rays. A radiation detection probe system is configured to find the sentinel lymph node, then identify and show the location of the hidden lesion, such that the boundary site can be evaluated during surgery. In the surgical treatment of parathyroid diseases as well as various malignant tumors such as breast cancer, melanoma, and colon cancer, it is possible to provide necessary information to a surgeon in real time. Due to these characteristics, which have been proved in many previous studies, the use of gamma probe technology is enormously expanding. However, applying the gamma probe to an intravascular procedure for determining the location of the balloon in the balloon catheter has not been studied.

SUMMARY

The present inventors have studied and tried to overcome the disadvantages entailed in the method of determining the location of the balloon catheter using X-rays, and consequently, have developed a technology that allows determination of an in vivo location of the balloon catheter from outside the body by including a radioactive isotope as an active ingredient in a balloon inflation composition used to inflate the balloon of the balloon catheter, then the present invention has been completed on the basis of the development.

Accordingly, an object of the present invention is to provide a balloon inflation composition which allows accurate and safe determination of the location of the balloon catheter inserted into the body from outside the body without using X-rays by including a radioactive isotope as an active ingredient.

Another object of the present invention is to provide a system for in vivo location determination of a balloon catheter having a new structure, which has high availability and high diagnostic accuracy, is safe due to low radiation exposure, and is easy to move without requiring expensive equipment, by using a radioisotope detector capable of inflating a balloon of the balloon catheter inserted into the body with a balloon inflation composition including a radioactive isotope, and easily detecting radiation radiated from the radioactive isotope contained in the inflated balloon from outside the body.

The object of the present invention is not limited to the above-described objects, and even if not explicitly mentioned, other objects of the invention that can be recognized by those skilled in the art from the detailed description of the invention to be described below will naturally be included in the present invention.

To achieve the above objects, according to an aspect of the present invention, there is provided a system for in vivo location determination of a balloon catheter including: a detector configured to detect proximity of a radioactive material; a guide wire provided to be inserted into a body; an intermediate member which has a radioactive material detected by the detector, and is configured to be inserted into the body along the guide wire to set an insertion length at which the radioactive material is detected by the detector; and a balloon catheter which is inserted into the body along the guide wire, and is inserted into the body by the set insertion length.

The intermediate member may be configured to be removed from the guide wire after setting the insertion length.

The balloon catheter may be inserted into the body by the set insertion length along the guide wire after the intermediate member is removed from the guide wire.

The balloon catheter may include: a tube having a hollow portion through which the guide wire and the intermediate member pass; and a balloon member provided to be inflatable on the tube.

The detector may include: a probe located on a target site outside the body to detect radiation radiated from the radioactive material; and a console unit configured to receive a detection signal from the probe and display a measurement result.

The radioactive material may be fixedly disposed in the intermediate member.

According to the above-described balloon inflation composition of the present invention, by including the radioactive isotope as an active ingredient, it is possible to accurately and safely determine the location of the balloon of the balloon catheter inserted into the body without using X-rays.

In addition, according to the system for in vivo location determination of a balloon catheter in the present invention, by using the radioisotope detector capable of inflating the balloon of the balloon catheter inserted into the body with the balloon inflation composition including a radioactive isotope, and easily detecting radiation radiated from the radioactive isotope contained in the inflated balloon from outside the body, the system has high availability and high diagnostic accuracy, is safe due to low radiation exposure, and is easy to move without requiring expensive equipment.

These technical effects of the present invention are not limited to the above-described range, and even if not explicitly mentioned, effects that can be recognized by those skilled in the art from the description of specific details for implementation of the invention to be described below are naturally included in the present invention.

DETAILED DESCRIPTION

Figures 1A, 1B:
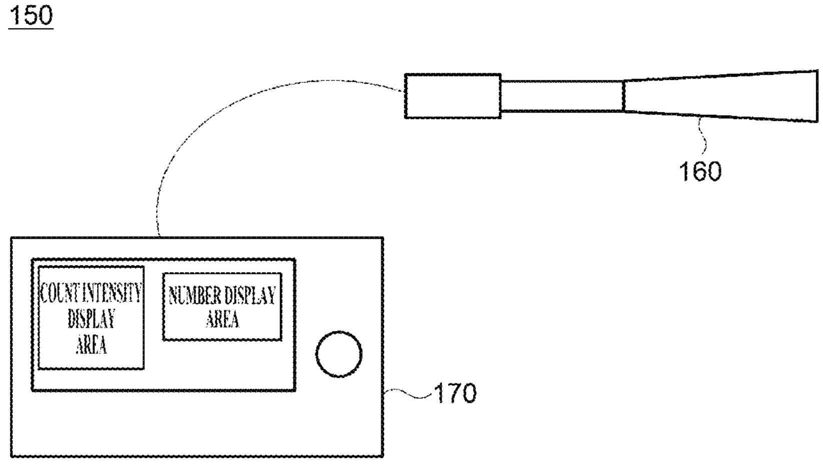
FIG. 1A is a schematic view illustrating an embodiment of a balloon catheter including a balloon inflation composition included in the system for in vivo location determination of a balloon catheter according to an embodiment of the present invention.
FIG. 1B is a schematic view illustrating an embodiment of a radioisotope detector included in the balloon inflation composition of the balloon catheter.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Further, the terms including numerals such as "first," "second," etc. in the present disclosure may be used to explain different components, but such components are not limited thereto. These terms are used only to distinguish one component from other components. For example, a first component may also be named a second component without departing from the scope of the present invention. Likewise, the second component may also be named the first component.

Unless otherwise defined, all terms including technical and scientific terms used herein have the same meaning as commonly understood by one of ordinary skill in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In interpreting the components, it is interpreted as including an error range even if there is no explicit description. In particular, when using the terms “about” or “substantially,” etc., which represents a level, it may be interpreted as being used in or close to that value when manufacturing and material tolerances specific to the mentioned meaning are presented.

In the case of a description for a temporal relationship, for example, when describing a temporal predecessor relationship such as ‘after -,’ ‘followed by -,’ ‘- after,’ ‘before -’, etc., it may include cases that are not continuous unless the terms ‘immediately’ or ‘directly’ are used.

Hereinafter, exemplary embodiments of the present invention will be described in detail with reference to the accompanying drawings.

However, the present invention may be embodied in many different forms and should not be construed as limited to the exemplary embodiments set forth herein. In the entire drawings, like reference numerals used for describing the present invention throughout the specification denote like elements.

A technical characteristic of the present invention is a system for in vivo location determination of a balloon catheter including: inflation composition which allows accurate and safe determination of the location of the balloon catheter inserted into the body from outside the body without using X-rays by including a radioactive isotope as an active ingredient; and a radioisotope detector capable of inflating a balloon of the balloon catheter inserted into the body with the balloon inflation composition including a radioactive isotope, and easily detecting radiation radiated from the radioactive isotope contained in the inflated balloon from outside the body.

That is, according to the present invention, since the location of the balloon may be determined by a detector for detecting radiation radiated from a radioactive material from outside the body, the accuracy of diagnosis may be secured compared to the existing method using the external boundary mark, and since it is easy to move the equipment and the system does not require expensive equipment, it is highly available in emergency bleeding situations compared to the conventional method using X-rays. The reason is that the radiation exposed to the patient and the operator is increased in the method using fluoroscopy depending on the amount of use, but the system of the present invention is safe since a small amount of radioactive isotope is used.

Therefore, the balloon inflation composition for in vivo location determination of a balloon catheter of the present invention includes the radioactive isotope as an active ingredient. A content of radioactive isotope contained in the balloon inflation composition may be included in an amount at which radiation is emitted at an intensity of 0.001 cps to 99.999 cps. The reason is that if the radioactive isotope is included in less than the amount at which the radiation is emitted at an intensity of 0.001 cps, the intensity of the radiation is so weak that the radioactive isotope contained in the balloon of the balloon catheter inserted into the body cannot be detected by the radioisotope detector from outside the body, and thereby it is not possible to determine the location of the balloon catheter. If the radioactive isotope is contained in more than the amount at which the radiation is emitted at an intensity of 99,999 cps, the intensity may be too large and thereby decrease a detection rate of the device due to an increase in the dead time between device readings.

As the radioactive isotope included in the balloon inflation composition of the present invention, any radioactive isotope may be used as long as it is permitted for medical use by the Ministry of Food and Drug Safety in Korea, and can emit beta particles and gamma particles. In one embodiment, it may be any one or more radioactive isotopes selected from the group consisting of 99 mTc, 18F, 123I, and 131I. The balloon inflation composition of the present invention may be formed in any one of liquid, gaseous, gel, and solid phases. When the balloon inflation composition is in the liquid phase, it may be formed by including a certain amount of radioactive isotope in physiological saline, is in the gaseous phase, it may be formed by including a certain amount of radioactive isotope in a gas allowed for medical use, and is in the gel phase, it may be formed by including a certain amount of radioactive isotope in a gel allowed for medical use. In addition, when the radioactive isotope is formed in the solid phase, it may be applied to all medical devices to be inserted into the body. For example, a radioactive isotope prepared in a solid phase may be located in a catheter, or may be located in a balloon portion of the balloon catheter. In addition, the radioactive isotope prepared in the solid phase may be located in a separate member to be inserted into the body.

The radioactive isotope may be included in the balloon inflation composition, but it is not limited thereto. Operations of the balloon member in a deflated state and an inflated state thereof may be performed separately. As long as the radioactive isotope is located in the catheter device, satisfactory operation of the balloon member may be obtained. The radioactive isotope may be formed in any one of liquid, gaseous, gel, and solid phases.

Next, the system for in vivo location determination of a balloon catheter of the present invention includes: a balloon inflation composition for in vivo location determination of balloon the catheter including a radioactive isotope; a balloon catheter including a balloon which is inflated by the balloon inflation composition while being inserted into the body; and a radioisotope detector configured to detect radiation radiated from the radioactive isotope from outside the body.

Herein, since the balloon inflation composition is the same as described above, only the balloon catheter and the radioisotope detector will be described with reference to FIGS. 1A and 1B.

As a balloon catheter 110 included in the system of the present invention, as shown in FIG. 1A, all known types of catheters may be used as long as they are catheters having a balloon member 120 mounted at a tip thereof. That is, as an inflation composition used by a doctor to insert the balloon catheter 110 into the body for a specific purpose and inflate the balloon at the tip, a balloon inflation composition 130 including a certain amount of radioactive isotope as in the present t invention may be inserted.

In addition, as shown in FIG. 1B, a radioisotope detector 150 included in the system of the present invention may detect radiation such as an alpha ray, beta ray, or gamma ray, which is emitted from the radioactive isotope, that is, a radioactive material, or a material having the radioactive isotope. As an example, a gamma particle detector 150 may be used. As shown in FIG. 1B, the gamma particle detector 150 may include a gamma probe 160 and a console unit 170.

The gamma probe 160 is a component configured to detect gamma particles emitted from the radioactive isotope, and the console unit 170 is a component configured to display measurement conditions and measurement results such as count. However, the detector for detecting radiation radiated from the radioactive material is not limited thereto. For example, PET or SPECT, which determines radiation emitted from the radioactive material by an image, may be applied to the detector. Further, an ionization box, a proportional counter, a Geiger-Müller counter tube, a scintillation counter, a semiconductor detector, etc., which detect radiation signals emitted from the radioactive material, may be applied to the detector.

As shown in FIG. 1A, when the balloon inflation composition 130 including a certain amount of radioactive isotope is inserted into the balloon of the balloon catheter, the location of the balloon catheter 110 inserted into the body may be accurately and quickly predicted by the radioisotope detector 150 having the structure shown in FIG. 1B.

Figure 2A:
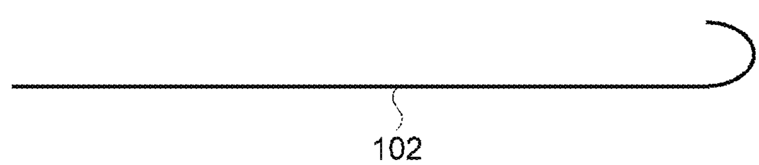
FIGS. 2A, 2B and 2C are views illustrating a catheter device according to an embodiment of the present invention.
Figure 2B:
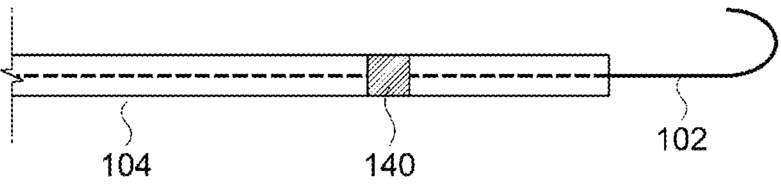
Figure 2C:
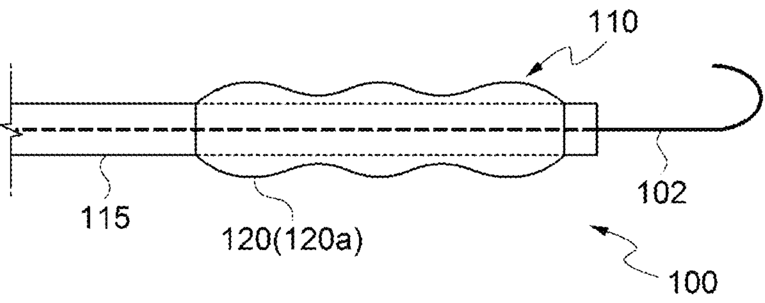

FIGS. 2A, 2B and 2C are views illustrating a catheter device according to an embodiment of the present invention. FIGS. 3A, 3B, 3C and 3D are views illustrating operations when the catheter device according to an embodiment of the present invention is inserted into the body.

A catheter device 100 may be provided to be inserted into the body. In the present invention, as an example, the catheter device 100 having the balloon member will be it not limited thereto. As an described, but is intermediate member 104, any known member is satisfactorily used as long as it can be inserted into the body while the radioactive material 140 is disposed therein.

The catheter device 100 may include a guide wire 102 and the balloon catheter 110. The catheter device 100 may be inserted into the body along a blood vessel V.

The guide wire 102 may be provided to guide the movement of the balloon catheter 110 which will be described below. The guide wire 102 may be made of a material having elasticity and flexibility. The guide wire 102 may be inserted so that the tip thereof can reach a target site in the body.

The catheter device 100 may include then intermediate member 104. The intermediate member 104 is movable along the guide wire 102. Since the intermediate member 104 has a hollow portion formed therein, the intermediate member 104 may be inserted into the body along the guide wire 102 so that the guide wire 102 passes through the hollow portion.

The intermediate member 104 may include radioactive isotopes. In the preceding description, it has been described that the balloon inflation composition 130 includes a certain amount of radioactive isotope. However, as described above, it is not limited thereto, and operations in the deflated state 120*a* and the inflated state 120*b* of the balloon member 120 may be performed separately. As long as the radioactive isotope is located in the catheter device 100, satisfactory operation of the balloon member may be obtained. Radioactive isotopes may be termed radioactive material 140.

The radioactive material 140 may be fixedly located at the intermediate member 104. The radioactive material 140 is located in the intermediate member 104, and radiation radiated from the radioactive material 140 is detected by the gamma probe 160, thereby detecting the intermediate member 104 moving to a target site.

While moving along the guide wire 102, the intermediate member 104 may be inserted into the body or blood vessel to a position where radiation radiated from the radioactive material 140 is detected. The intermediate member 104 may be provided to check a length of the radioactive material 140 inserted into the blood vessel to the position where radiation radiated therefrom is detected. For example, the intermediate member 104 may include a plurality of scales which are arranged in a longitudinal direction in order to determine the inserted length. The intermediate member 104 may set the insertion length. The insertion length of the intermediate member 104 may be set to a length into which the balloon catheter 110, which will be described below, is inserted. The insertion length of the balloon catheter 110 may be set by the intermediate member 104.

The balloon catheter 110 is movable along the guide wire 102. Since the balloon catheter 110 has a hollow portion formed therein, the balloon catheter 110 may be inserted into the body along the guide wire 102 so that the guide wire 102 passes through the hollow portion.

The balloon catheter 110 may be inserted into the body by the insertion length set by the intermediate member 104 as described above. Thereby, the balloon catheter 110 may be accurately located at the target site. After the intermediate member 104 is removed from the guide wire 102, the balloon catheter 110 may be inserted into the body along the guide wire 102. However, it is not limited thereto, and the balloon catheter 110 may have a hollow portion through which the guide wire 102 and the intermediate member 104 pass, and may be inserted into the body along the guide wire 102 and the intermediate member 104.

The balloon catheter 110 may include a tube 115 and the balloon member 120, and may have a long length formed enough to be sufficiently connected to the target site from the outside the body. The above-described hollow portion may be formed in the tube 115.

The balloon member 120 may be provided on the tube 115. The balloon member 120 may be provided to be operated in a deflated state 120*a* and an inflated state 120*b*. During when the balloon catheter 110 moves in the body, the balloon member 120 may be operated in the deflated state 120*a*. When the balloon member 120 of the balloon catheter 110 is located at the target site, the balloon member 120 may be operated in the inflated state 120*b*. The balloon member 120 may press the blood vessel V where bleeding occurs by an outer surface thereof in the inflated state 120*b*. Thereby, the balloon member 120 may prevent or reduce the bleeding occurring in the blood vessel V.

Hereinafter, operations of the system for in vivo location determination of a balloon catheter according to the present invention will be described with reference to FIGS. 3A to 3C.

Figure 3A:
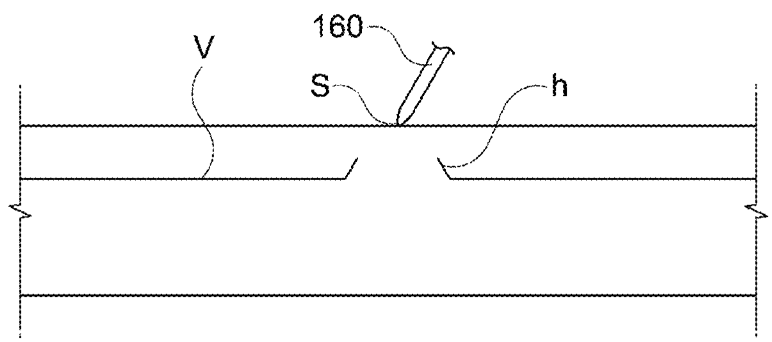
FIGS. 3A, 3B, 3C and 3D are views illustrating operations when the catheter device according to an embodiment of the present invention is inserted into the body.

As shown in FIG. 3A, when bleeding occurs in the blood vessel V in the body, a bleeding site h may be detected through the test. The gamma probe 160 may approach an external portion S corresponding to the bleeding site h.

Figure 3B:
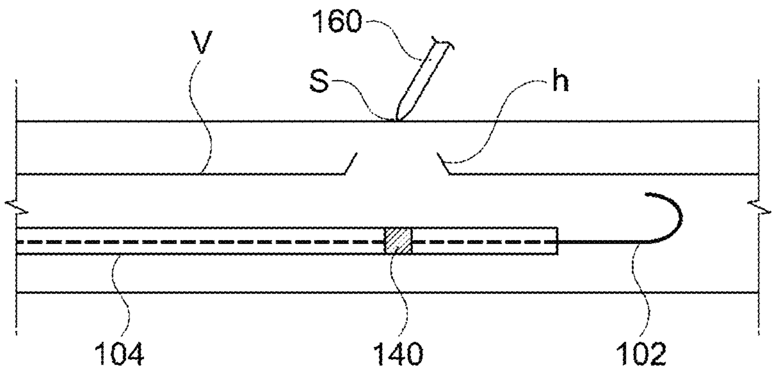

As shown in FIG. 3B, the guide wire 102 is first inserted along the blood vessel. Then, the intermediate member 104 including the radioactive material 140 is inserted along the guide wire 102.

An example, in which the gamma probe 160 accesses the external portion S before inserting the guide wire 102, has been described, but it is not limited thereto. After the guide wire 102 is inserted, the gamma probe 160 may access the external portion corresponding to the process of inserting the intermediate member 104.

When the radioactive material 140 is adjacent to the gamma probe 160, it can be seen that the intermediate member 104 has moved to a bleeding site h through an alarm or signal from the detector 150.

At this time, a length into which the intermediate member 104 is inserted may be determined. That is, the length into which the intermediate member 104 is inserted may be determined from the outside the body. This length may be set as the insertion length.

Figure 3C:
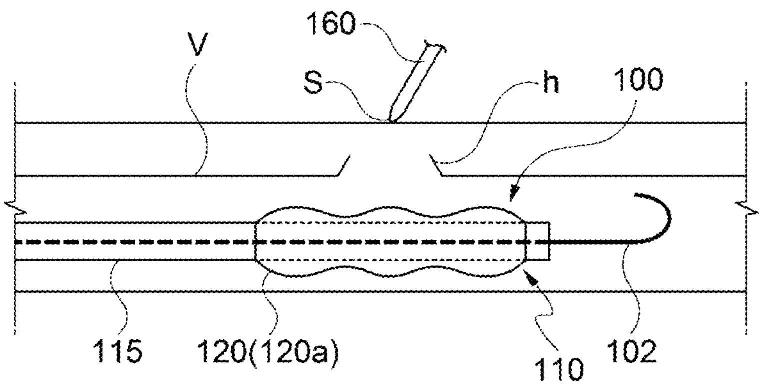

Thereafter, as shown in FIG. 3C, the balloon catheter 110 is inserted by the set insertion length. In inserting the balloon catheter 110, after the intermediate member 104 is removed leaving the guide wire 102, the balloon catheter 110 may be inserted. However, it is not limited thereto, and the balloon catheter may be inserted along the guide wire 102 and the intermediate member 104 so that the intermediate member 104 passes through the hollow portion of the balloon catheter 110. When the balloon catheter 110 is inserted by the set length, the balloon member 120 of the balloon catheter 110 is located at the bleeding site h.

Figure 3D:
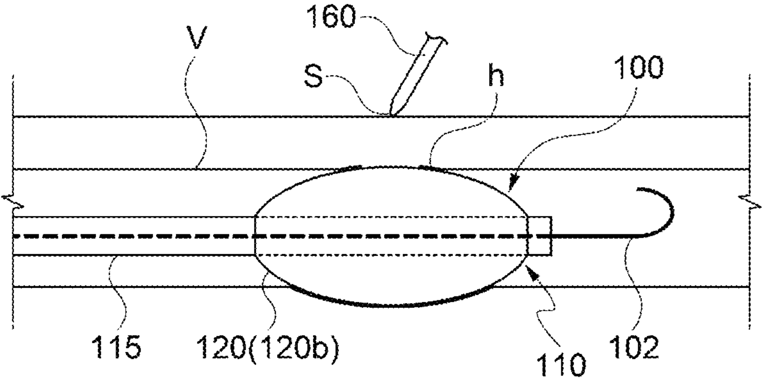

Thereafter, as shown in FIG. 3D, the balloon member 120 is operated in the inflated state 120*b*, thereby the bleeding may be stopped or reduced by pressing the bleeding site h with the outer surface thereof.

As described above, the gamma particle detector 150 used in the system of the present invention has costs of device much lower than the fluoroscopy method, and is portable with a small size. Therefore, the system of the present invention may also be used to determine the location of the balloon of an aortic occlusion in an operating room by moving it to the operating room. In addition, as will be described below, since the gamma probe is very easy to handle, determining the location does not greatly depend on the skill or experience of the operator. Therefore, there is an advantage of not requiring special training or taking a lot of time to handle the gamma probe. In the experimental examples to be described below, two surgeons who had 10 years of experience as surgeons, but had no experience handling the gamma probe, participated. However, the surgeons learned how to use the gamma probe very quickly, and the experimental results showed that there was no difference in the number of failures, difference in a distance between the expected position of the balloon and the actual position of the balloon, and the time it took to perform the study. This shows that the system of the present invention including the gamma probe is not greatly affected by the specific skills or experience of the surgeon who handles the gamma probe, and is an easy-to-use tool.

Example 1

A balloon inflation composition was prepared by adding 37 mlq of 99 mTc-pertechnetate to 8 ml of normal saline.

Example 2

A system for in vivo location determination of a balloon catheter was implemented by using the balloon inflation composition prepared in Example 1, a balloon catheter (REBOA RB-167080-E, Tokai Medical, Aichi, Japan) and a gamma probe (Neoprobe 2000; Neoprobe Corp, Dublin, Ohio, USA).

Experimental Example

Evaluation was performed as follows to confirm whether the gamma probe may guide and determine the location of the balloon catheter using REBOA in a human blood vessel phantom using the system for in vivo location determination of a balloon catheter implemented in Example 2, and whether the system of the present invention is easy to use by comparing abilities to search for the balloon of the balloon catheter two surgeons who have no experience of using the gamma probe.

1. Material and Method (1) Material (Phantom)

Figure 4:
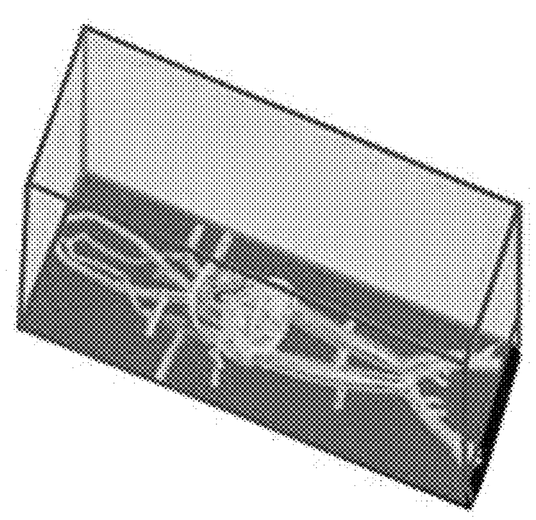
FIG. 4 is schematic views for determining whether the location of the balloon catheter can actually be confirmed using the system for in vivo location determination of a balloon catheter previously illustrated, wherein (A) is a schematic view of a phantom, and (B) is a photograph illustrating a gamma probe set for an experiment in a nuclear medicine imaging room.
Figure 4:
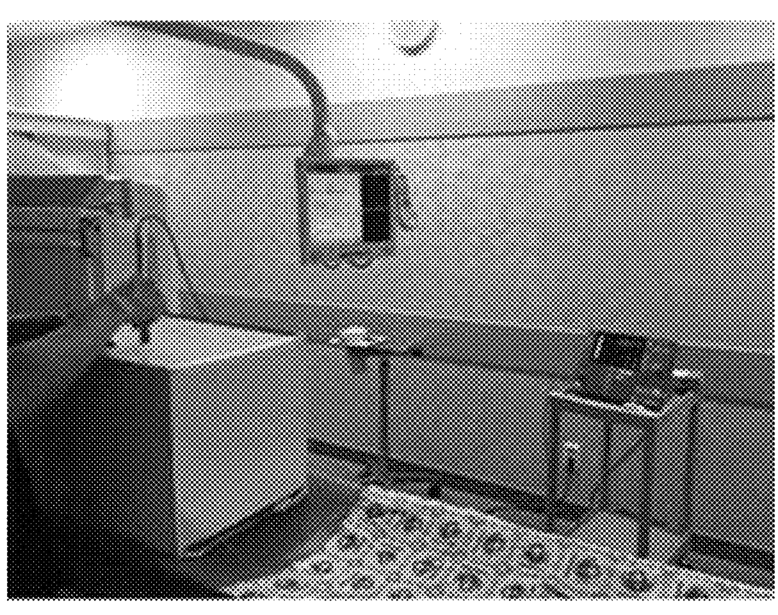

An interstitial model LLC (Plymouth, MN, USA) was purchased to be used inside of the phantom. This educational simulator (Bilateral Bob Plus, BB-6050) is a model which was made by mimicking the arterial and venous structures of an adult male having an average size, and was made for practice skills in the installation, insertion and management of the catheter, the guide wire and the balloon catheter. An outer shell of the phantom was composed of a skin-colored mat board having a size of 300 mm (W)×600 mm (L)×300 mm (H) and a thickness of 5 mm. When covering a lid, as shown in (A) of FIG. 4, all surfaces of a right-angled parallelepiped are blocked except for a small gap for approaching both iliac sheath ports at the bottom of the outer shell.

(2) Experimental Design

An assistant and two surgeons with 10 years of experience participated in the study. To ensure objectivity, after the assistant prepared the study in a nuclear medicine imaging room, each surgeon entered the room to conduct the study.

The balloon catheter used in the system of the present invention was moved forward by the assistant to an aortic zone I or zone III at any location. Then, the balloon inflation composition prepared in Example 1 was added to inflate the balloon, and after covering the outer shell of the phantom, the surgeon made the assistant enter the laboratory (see (B) of FIG. 4).

After the preparation for the experiment was completed, each surgeon entered the nuclear medicine imaging room to find the location of the balloon, set it appropriately for 99 mTc energy, and searched for the location of the balloon using the gamma probe of the system of the present invention. When the gamma probe was close to the balloon, a beep was heard from the console unit, and the count was specified high. When the beep of the detector becomes stronger and the count is increased, it means that the gamma probe is located at a short distance from the balloon including 99 mTc-pertechnetate. Each surgeon predicted the position of the inflated balloon, and placed a gamma-ray point light source having a diameter of 3 mm on the outer shell of the phantom, thereby selecting the point with the highest warning sound and count as a prediction point. Then, the assistant recorded the count and the time taken, each of which was defined as one time, and this process was repeated 20 times for each surgeon in both aortic zone I and zone III.

(3) Determine the Location of the Balloon

The predicted and actual positions of the balloon were determined using a hybrid SPECT/CT imaging system (Discovery NM/CT 670, GE Healthcare). In each experiment, a 10 second lateral planar image was acquired on a 256×256 matrix having a 20% window centered around a 140 keV optical pickup using a low energy, high resolution parallel collimator. SPECT/CT was taken every 10 times, and a 5 second/30 degree step and shoot protocol was used for a total of 12 views per camera head. CT was performed immediately after obtaining SPECT. Parameters included a current of 40 mA, a voltage of 140 kV, and a 3.75 mm slice reconstructed into a 512×512 matrix.

Figure 5:
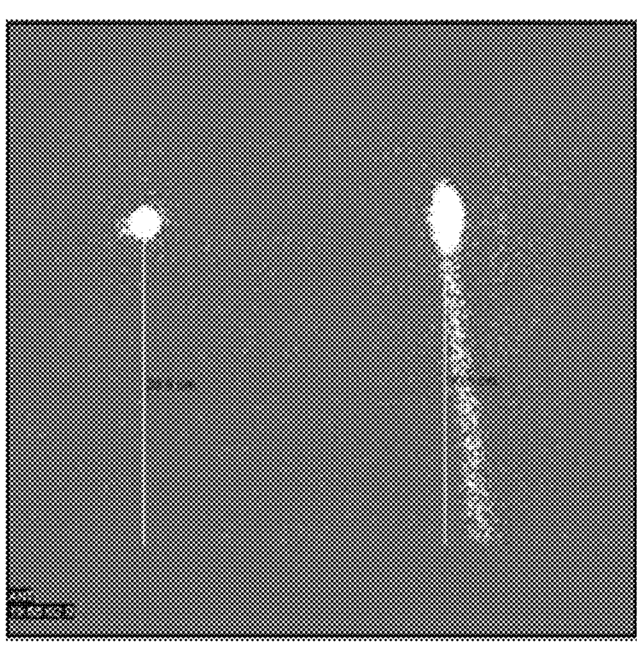
FIG. 5 is representative plane images for measuring a distance between a location of the balloon predicted at a lower boundary of the phantom and the actual location of the balloon in zone I (A) and zone III (B) measured in the experiment set as shown in FIG. 4.
Figure 5:
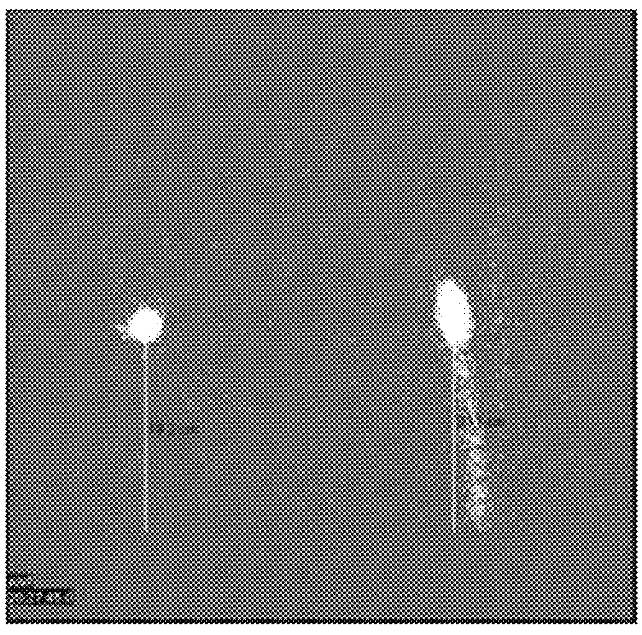

All planar and SPECT/CT images were analyzed at a Xeleris workstation (GE Healthcare). Distances to the center of the gamma ray point source or the catheter balloon was measured in each image. The predicted distance was defined as a distance from a lower boundary of the plane image to the center of the gamma ray point source, and the actual distance was defined as a distance from the lower boundary of the plane image to the center of the catheter balloon (see FIG. 5). A difference in the distance between the predicted part and the actual part was calculated as an absolute value of the actual balloon part minus the predicted part. As shown in FIG. 5, if a gamma-ray generation source is located within the length of the inflated balloon, it is classified as a success, and if the gamma-ray generation source is located outside the inflated balloon, it is classified as a failure.

(4) Statistical Analysis

Continuous variables were expressed as mean±standard deviation (SD), and categorical variables were expressed as frequencies and percentages. In order to compare the distances of the aortic zones with two surgeons, a t-test was used, and results thereof were estimated using Fisher's exact test. P values less than 0.05 were considered statistically significant, and analysis was performed using SPSS version 21.0 (IBM Corp., Armonk, NY, USA).

2. Results

1. Research Results of Zone I and Zone III

In order to predict the location of the balloon, two operators performed a total of 80 experiments, 20 times each in zone I and zone III. Two operators failed 3 times in zone I and failed 4 times in zone III. A difference in the distance from the actual position of the balloon was 1.40±1.40 cm in zone I and 1.56±1.15 cm in zone III. A difference in the distance between the actual site and the predicted distance of the balloon was not significantly different between zone I and zone III. However, the time taken to search for the location of the balloon was longer in zone I (2.68±1.31 minutes) than in zone III (2.05±1.08 minutes). In addition, the count of the balloon measured by the gamma probe was larger in zone I than in zone III.

2. Comparison of Study Results Between Two Surgeons

Figure 6:
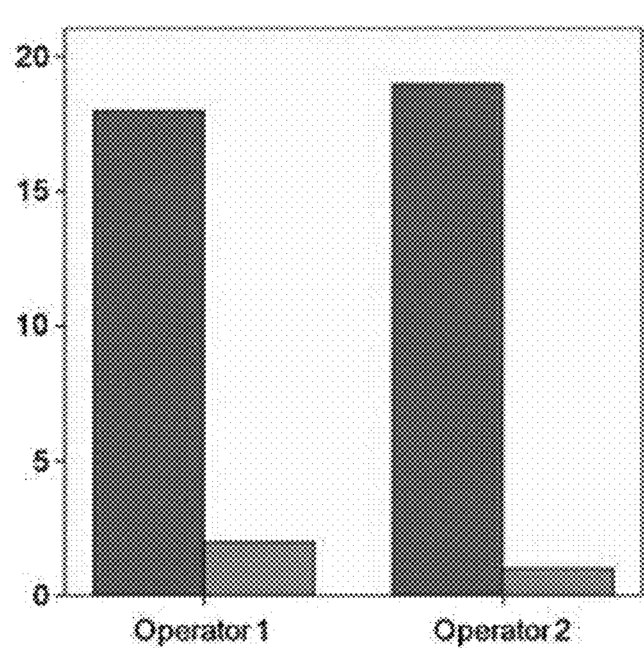
FIG. 6 is graphs illustrating frequencies of success and failure in predicting the location of the balloon in zone I (A) and zone III (B) measured in the experiment set as shown in FIG. 4.
Figure 6:
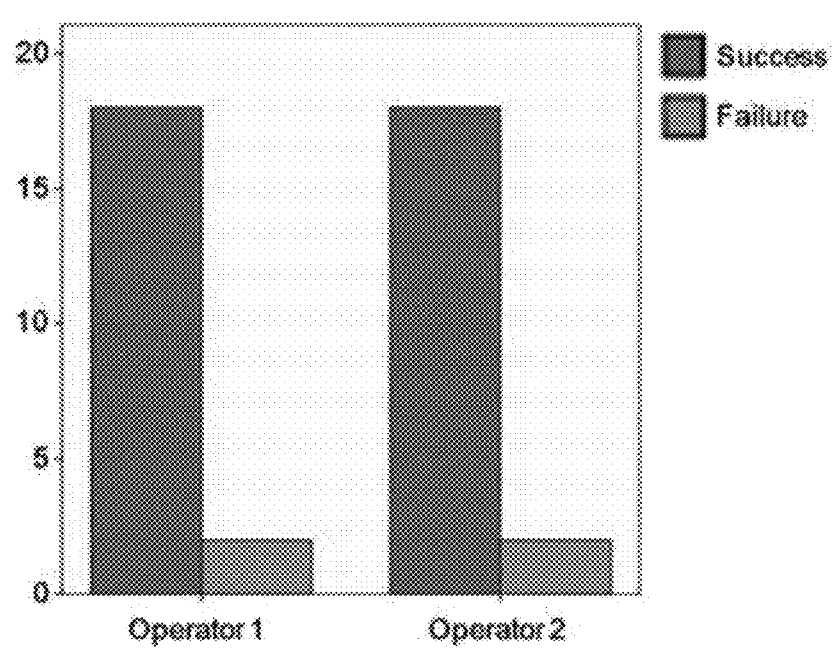
Figure 7:
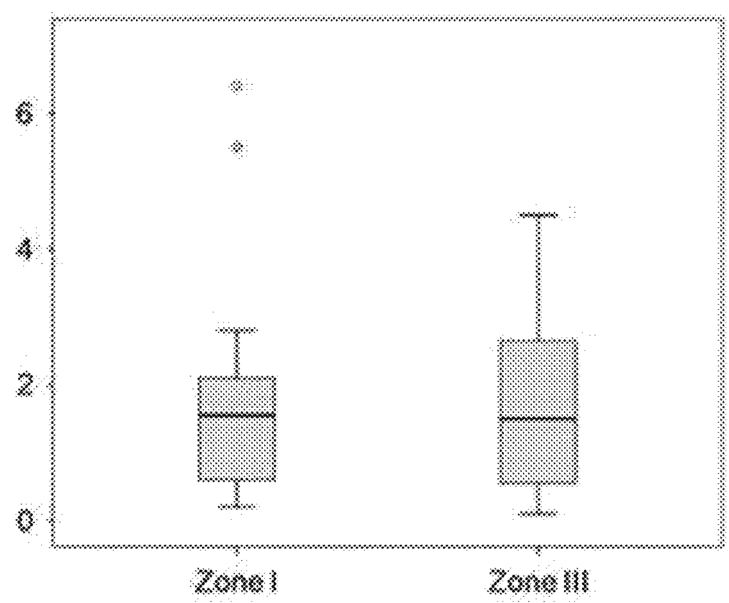
FIG. 7 is graphs illustrating a difference in a distance (cm) between positions predicted by Experimenter 1 (A) and Experimenter 2 (B) in the experiment set as shown in FIG. 4.
Figure 7:
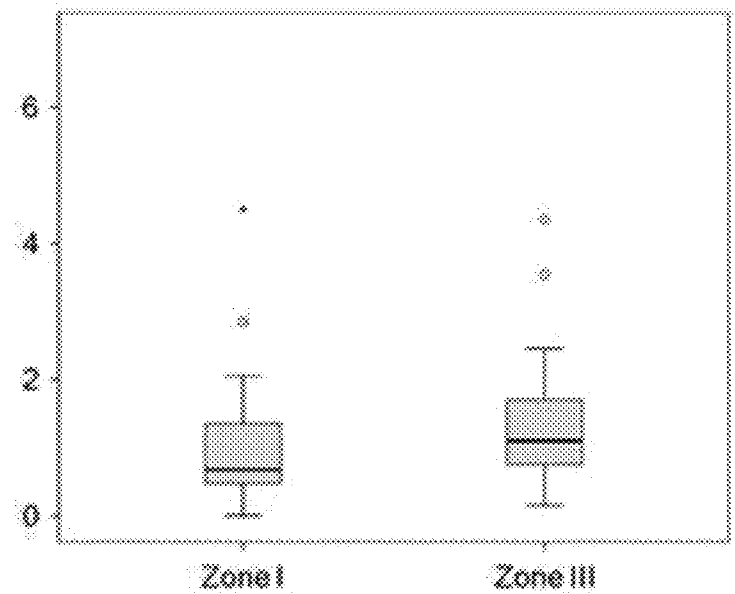

Surgeon 1 failed twice in zone I and twice in zone III. Surgeon 2 failed once in zone I and twice in zone III (FIG. 6). However, the number of failures did not differ between the two surgeons. Although the difference in distance between the positions of the balloon predicted by surgeon 1 was greater than that of surgeon 2, there was no difference between the two surgeons in both zone I and zone III (FIG. 7). Surgeon 1 took more time to locate the balloon in both zones I and III, but the difference was not statistically significant. The balloon count measured with a gamma probe was higher in surgeon 2 than in surgeon 1.

3. Comparison of Research Results Between Success and Failure

There were 73 success cases (91%) and 7 failure cases (9%) in the entire study. The distance difference was longer in the case of failure (4.66±0.99 cm) than the case of success (1.17±0.79 cm). As a result of measuring by the gamma probe, the successful cases were slightly higher than the failed cases, but the difference between them was not statistically significant. Although it took more time to search for the location of the balloon in the failed cases than in the successful cases, the difference in time was also not statistically significant.

Figure 8:
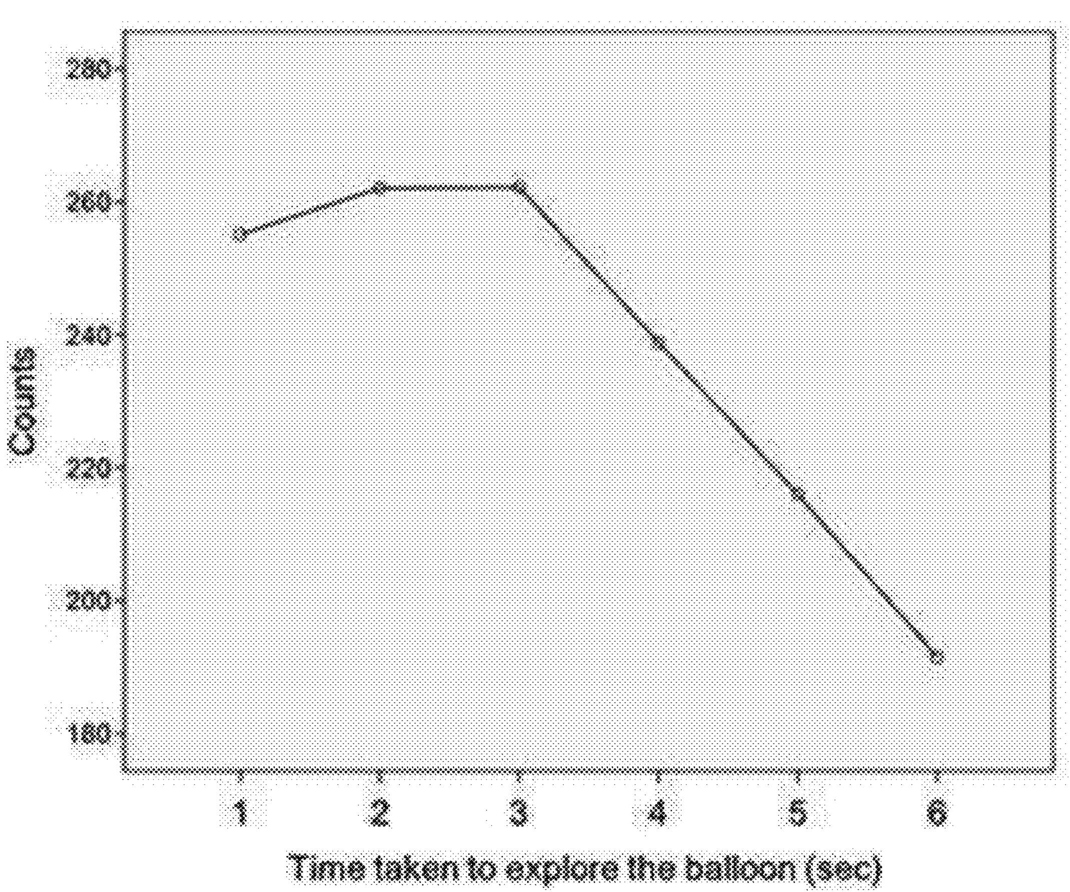
FIG. 8 is a graph illustrating a time taken to search for the location of the balloon measured in the experiment set as shown in FIG. 4 and the average coefficient measured by the gamma probe.

4. Relationship Between the Time Taken to Search for The Position of the Balloon and the Count Measured by the Gamma Probe (FIG. 8)

It took 1 second in 19 cases, 2 seconds in 34 cases, 3 seconds in 15 cases, 4 seconds in 5 cases, 5 seconds in 5 cases, and 6 seconds in 2 cases to search for the location of the balloon. FIG. 8 shows the number of cases according to the time it takes to search for the location of the balloon. There was a steep slope between 3 seconds and 4 seconds, and based on this, the cases were classified into two groups (a group of less than 3 seconds and a group of 3 seconds or more). Cases taking less than 3 seconds (260.10±51.05) showed higher count than the cases taking 3 seconds or more (221.42±38.94), and the difference between the two groups was not significant (p=0.015 by Student's test, and p=0.024 by Mann-Whitney U test).

From the above experimental results, when confirming the results by nuclear medicine images using the system of the present invention, the difference in the distance between the predicted location and the actual location of the balloon was 1.40 cm in zone I and 1.56 cm in zone III. The time taken to search for the location of the balloon using the gamma probe was 2.7 seconds in zone I and 2.1 seconds in zone III.

These results show that, when determining the location of the balloon of the balloon catheter inserted into the body using the system of the present invention including the gamma probe, not only the location of the balloon may be accurately predicted and the balloon may be quickly located within a short time, but also the results are less influenced by the operator, and exhibit that the system of the present invention has an advantage of being able to quickly determine the location of the balloon even when the patient has fragments and air. In addition, according to the present invention, it is predicted that information on the location of the balloon may be provided without fluoroscopy in the vascular procedures of trauma patients.

While the present invention has been described with reference to several preferred embodiments, the present invention is not limited to the above-described exemplary embodiments, and it will be understood by those skilled in the art that various modifications and variations may be made within the detailed description of the invention and accompanying drawings without departing from the scope of the present invention as defined by the appended claims, as well as these modifications and variations should be included in the scope of the present invention according to doctrine of equivalents.

What is claimed is:

1. A system for in vivo location determination of a balloon catheter, the system comprising:

a radiation detector including a hand bar type probe configured to detect radiation radiated from a radioactive material and to indicate, by a sound and a radioactive count, that the radioactive material is adjacent to the hand bar type probe, wherein as a distance between the hand bar type probe and the radioactive material becomes shorter, the sound becomes louder and the radioactive count increases;

a guide wire provided to be inserted into a body;

an intermediate member which has a first radioactive material detected by the radiation detector, and is configured to be inserted into the body along an outer diameter of the guide wire to set an insertion length for inserting a balloon catheter, wherein the set insertion length is determined based on a length of the intermediate member inserted up to a location of the first radioactive material, the first radioactive material being detected and indicated by the hand bar type probe positioned at an external portion of the body corresponding to a target site; and the balloon catheter configured to be inserted into the body along the outer diameter of the guide wire, and configured to be inserted into the body by the set insertion length determined based on the insertion of the intermediate member, and configured to be coupled to the guide wire, wherein the intermediate member has a first hollow portion through which the guide wire passes, wherein the balloon catheter comprises:

a tube having a second hollow portion through which the guide wire passes; and a balloon member filled with a balloon expansion composition in a fluid phase in which a second radioactive material is mixed and provided to be inflatable on the tube;

wherein the balloon member is configured to be coupled to the guide wire after the intermediate member is removed from the guide wire, the balloon member is inserted along the guide wire by the set insertion length, and wherein the first radioactive material and the second radioactive material include one or more radioactive isotopes that emit gamma rays or beta particles, the radioactive isotopes being selected from a group consisting of 99 mTc, 18F, 123I, and 131I.

2. The system of claim 1, wherein the radiation detector further comprises:

a console unit configured to receive a detection signal from the hand bar type probe and display a measurement result.

3. The system of claim 1, wherein the first radioactive material is fixedly disposed in the intermediate member.

* * * * *